United States Patent [19]

Van de Velde

[11] Patent Number: 6,000,799
[45] Date of Patent: Dec. 14, 1999

[54] MAXWELLIAN VIEW AND MODULATION CONTROL OPTIONS FOR THE SCANNING LASER OPHTHALMOSCOPE

[75] Inventor: Frans J. Van de Velde, Boston, Mass.

[73] Assignee: Jozef F. Van de Velde, Oosterzele, Belgium

[21] Appl. No.: 09/033,900

[22] Filed: May 1, 1998

[51] Int. Cl.$^6$ ...................................................... A61B 3/10
[52] U.S. Cl. .......................................................... 351/205
[58] Field of Search ........................... 351/200, 205, 351/206, 207, 208, 209, 210, 221, 246

[56] References Cited

U.S. PATENT DOCUMENTS

| | | | |
|---|---|---|---|
| 4,213,678 | 7/1980 | Pomerantzeff et al. | 351/206 |
| 5,568,208 | 10/1996 | Van De Velde | 351/221 |

*Primary Examiner*—George Manuel

[57] ABSTRACT

Maxwellian view and modulation control options for the scanning laser ophthalmoscope allow knowing, maintaining and systematically varying the entrance location of the Maxwellian view used for imaging or functional testing of a particular retinal test location. The scanning laser ophthalmoscope simultaneously images for subsequent digital image processing the anterior and posterior segment of the eye by using a second Newtonian imaging device or by repositioning the entrance location of the Maxwellian view in such way that vignetting of the anatomical pupil occurs. In the second method, the fixation target is systematically moved within the visible border of the anatomical pupil in order to use another entrance location of the Maxwellian view for a given retinal test location. The main advantages are simplicity of utility and the fact that the scanning laser ophthalmoscope no longer has to move in order to select or maintain a particular entrance location of the Maxwellian view for a given retinal test location.

4 Claims, 7 Drawing Sheets

MAXWELLIAN VIEW AND MODULATION CONTROL OPTIONS FOR THE SCANNING LASER OPHTHALMOSCOPE

CROSS REFERENCE TO RELATED APPLICATIONS

This application is relayed to U.S. Pat. No. 5,568,208, issued Oct. 22, 1996 entitled "Modified scanning laser ophthalmoscope for psychophysical applicatons".

BACKGROUND

1. Field of Invention

The invention relates in general to methods for examining the eye and specifically to the use of an electro-optical ophthalmoscope for imaging and psychophysical applications.

2. Description of Prior Art

The related U.S. Pat. No. 5,568,208, "Modified scanning laser ophthalmoscope for psychophysical applications", issued Oct. 22, 1996, discloses a scanning laser ophthalmoscope that is modified in order to know and control an important variable in psychophysical testing of the eye with the scanning laser ophthalmoscope, i.e. the entrance location of the Maxwellian view illumination or pivot point of the illuminating system of the scanning laser ophthalmoscope. For some psychophysical applications both the retinal location that is being tested and the entrance location of the Maxwellian view in the eye used for this testing have to be known, maintained or systematically varied according to an algorithmic design. In the prior art, this entrance location is determined with the help of a second imaging device that is attached to the scanning laser ophthalmoscope in a fixed position. A beamsplitter is usually employed to obtain a better frontal observation of the anterior segment of the eye. To acquire reference video images of the anterior segment prior to actual testing with this second imaging device, it is sufficient to focus on the iris, for example when the pivot point of the Maxwellian view, seen as a low intensity backscatter, is also in focus in different places on the anterior surface of the lens and iris. A harrier filter attached to the second imaging device and a wide angle third wavelength external light source facilitate the acquisition of reference images that contain supplementary anterior segment fiducial landmarks including Purkinje images of the light source, but do not contain any spurious reflexes from the scanning laser ophthalmoscope illuminating sources during testing. A two-dimensional normalized gray scale correlation or equivalent algorithm localizes unambiguously selected fiducial landmarks in the continuous stream of video images of the anterior segment of the eye, and calculates any displacement of the anterior segment relative to the pivot point of the Maxwellian view. Furthermore, a feedback loop, steering the positioning motors of the scanning laser ophthalmoscope, can then keep the pivot point of the Maxwellian view in the desired location within the anatomical pupil of the eye. This utility is highly beneficial. For example, when performing automated microperimetry on an extended area of the retina with the scanning laser ophthalmoscope, the pivot point of the Maxwellian view can be stabilized within the confines of the anatomical pupil, increasing the efficiency of the algorithms involved. Another psychophysical application that needs to know, maintain and systematically vary the entrance location of the Maxwellian view illumination is the measurement of Stiles-Crawford parameters or photopigment concentration for a specific retinal location. Two important limitations exist when reducing to practice the utility to control simultaneously the entrance location of the Maxwellian view and the retinal location being tested. First, variations in pupil size cannot be measured easily. These variations can also influence the efficiency and reliability of the two dimensional gray-scale correlation algorithms or their equivalent, since a change in pupil diameter is likely to change the aspect and position of some fiducial landmarks in the images of the anterior segment of the eye as well. Second, in order to adjust, maintain or systematically vary the entrance location of the Maxwellian view, it is necessary to move the scanning laser ophthalmoscope and subject relative to each other. This necessity increases the complexity of the equipment.

OBJECTS, ADVANTAGES AND SUMMARY OF THE INVENTION

In order to overcome the above mentioned restrictions for some psychophysical applications, alternative disclosures can be considered. The alternatives simplify the prior art utility or augment its capabilities:

1. If the pupil diameter is larger than the entrance location of the Maxwellian view illumination, the second imaging device can capture the diffuse backscatter of light inside the anatomical pupil of the eye. This light is derived from stronger scanning illuminating laser beams of the scanning laser ophthalmoscope after backscattering from the retina, and this light completely fills the anatomical pupil on the image of the anterior segment of the eye. The third wavelength external light source and barrier filters are then not used. This method is applicable when fluctuating pupil diameters are present and can easily quantify the anatomical pupil characteristics such as size, shape and location.

2. If the retinal location to be tested remains same and relatively close to the subject's fixation area in the course of a particular psychophysical test, and the only variable is the entrance location of the Maxweilian view used for that particular location, then the required systematic movement of the scanning laser ophthalmoscope relative to the subject can be replaced with simple rotational eye movements of the subject alone. An essential feature is the positioning of the pivot point of the Maxwellian view so that vignetting occurs of the anatomical pupil. The subject's fixation locus on the retina is then systematically varied within the confines of the anatomical pupil of the eye, thereby selecting a new entrance point of the Maxwellian view corresponding to the same retinal location. This technique is possible because the nodal point of the complete eye optics is several millimeters in front of the rotational center of the eye. The technique effectively replaces the systematic movement of the scanning laser ophthalmoscope relative to the subject with voluntary rotational eye movements of the eye. This method considerably simplifies the equipment and algorithms.

Other objects and advantages of the invention will become apparent from a consideration of the drawings and ensuing description.

A motor block component is capable of moving the SLO in the x-y-z directions.

Figure 1:
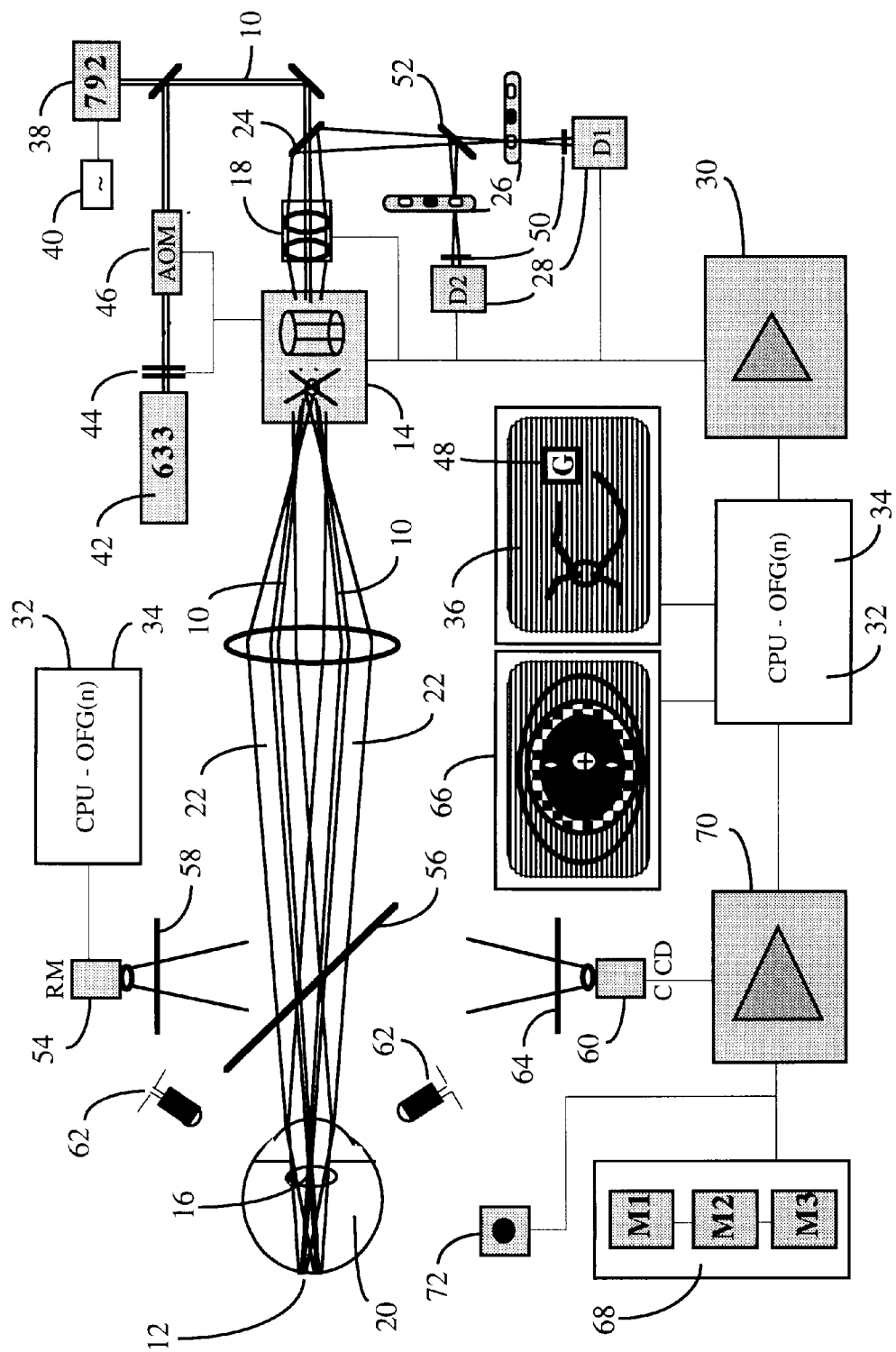
FIG. 1 is a review of the prior art of related U.S. patent. It illustrates a confocal scanning laser ophthalmoscope with several modulating means, to which is attached second Newtonian imaging device, beamsplitter, and third wavelength wide angle illumination source with appropriate filters. The anterior segment is visualized on the monitor devoid of spurious reflexes and shows a dark and dilated anatomical pupil with Purkinje images and overlay indicating location of pivot point of Maxwellian view illumination.
Figure 2:
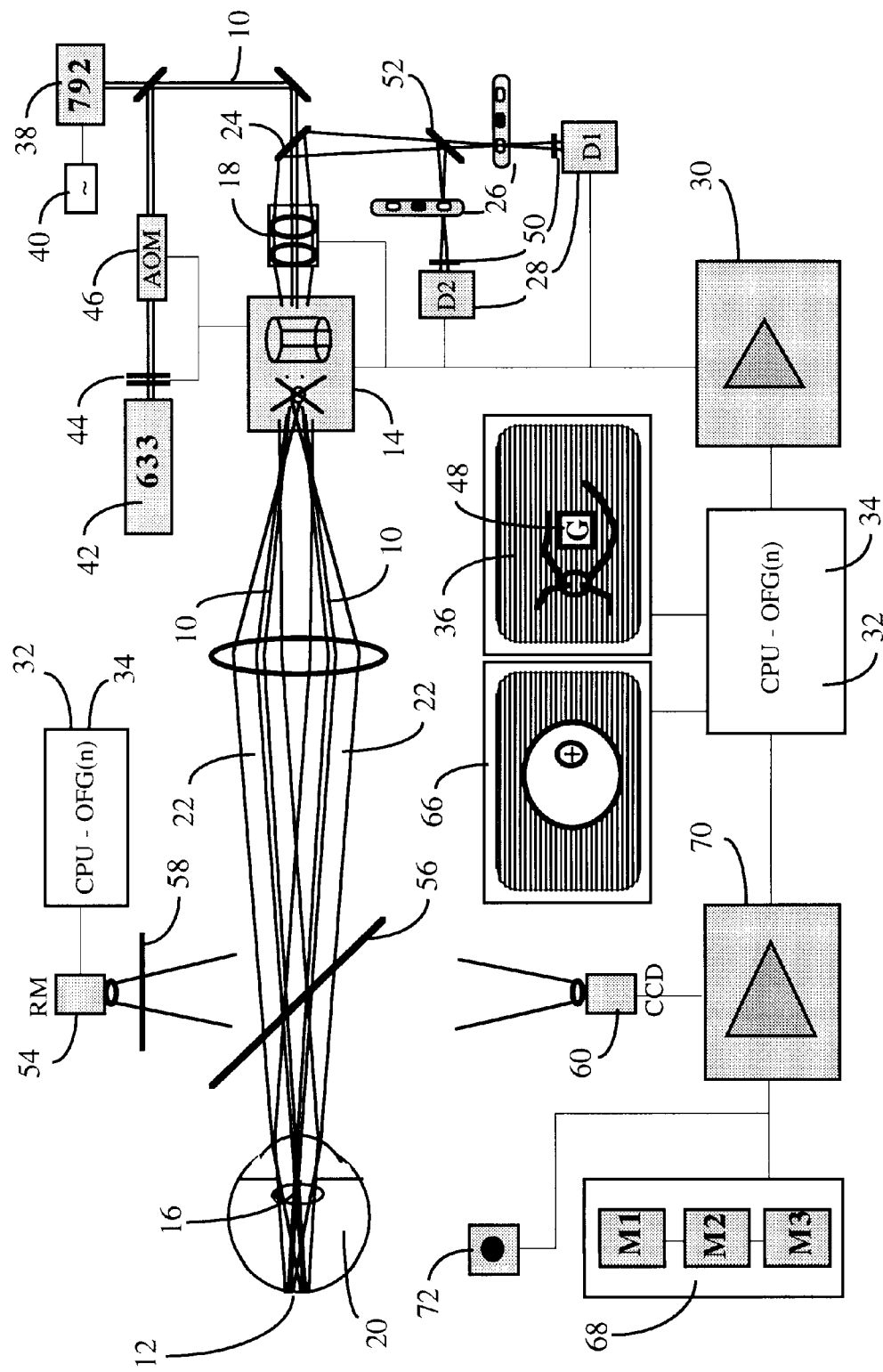

FIG. 2 illustrates a variation of FIG. 1 in which is noted the absence of the third wavelength wide angle external illuminating source and barrier filter. The monitor illustrates an anterior segment in which only the anatomical pupil is seen as a homogeneous white round object, in focus. The pupil size is variable. The pupil image itself conceals any spurious reflexes that may exist. The pupil diameter is larger than the entrance location of the Maxwellian view.

Figure 3:
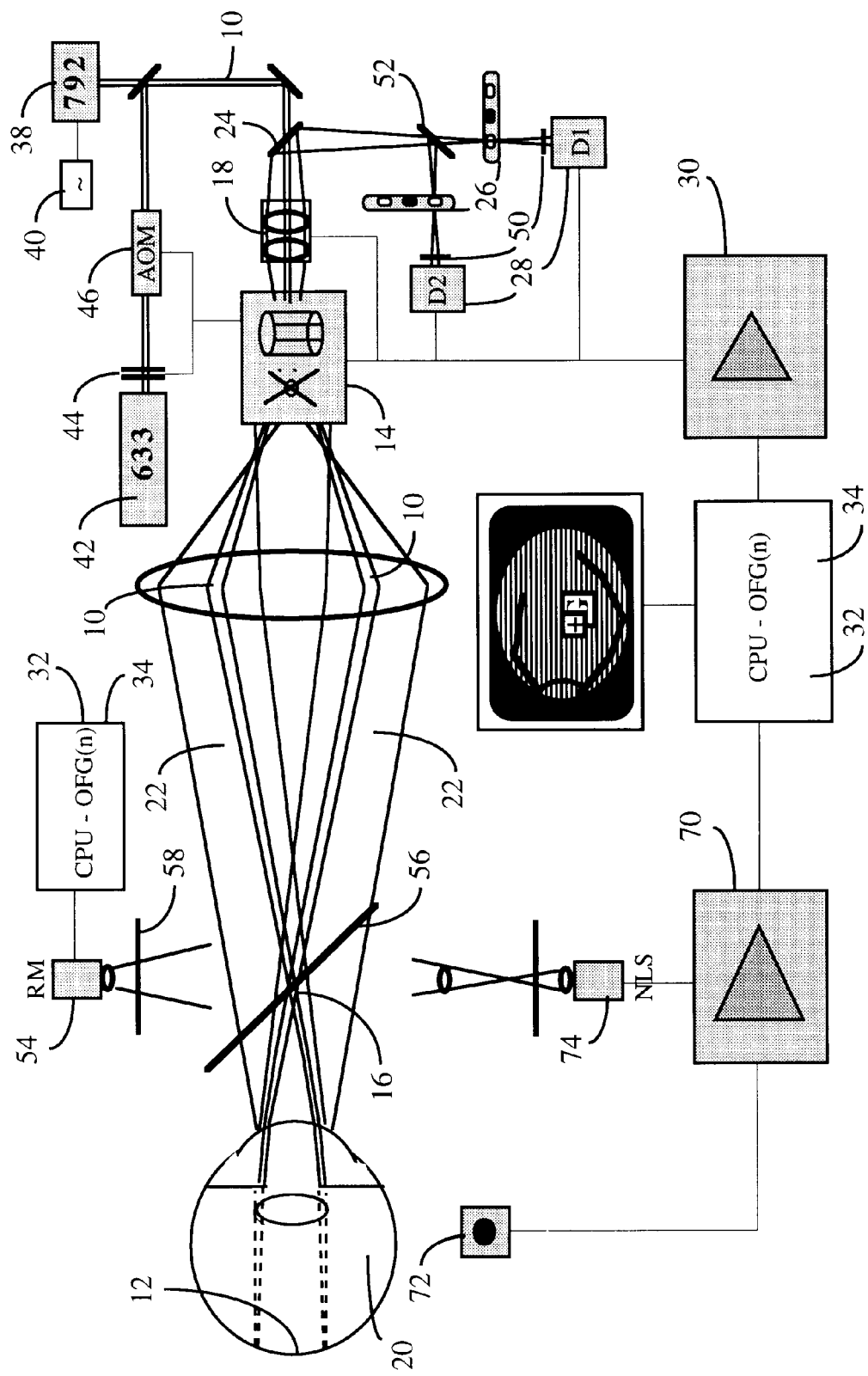

FIG. 3 illustrates another variation of FIG. 1 in which is noted the absence of the third wavelength wide angle external illuminating source and second Newtonian imaging device. The second Newtonian imaging device can be replaced, optionally, with a Newtonian regulated external light source for diffusely illuminating the anterior segment of the eye with a visible wavelength. Importantly, the pivot point of the Maxwellian view illumination of the scanning laser ophthalmoscope has been relocated anteriorly to the eye. Vignetting of the anatomical pupil is visible on the monitor. This anatomical pupil has a blurred margin and contains some retinal details. The motor block is absent.

Figure 4:
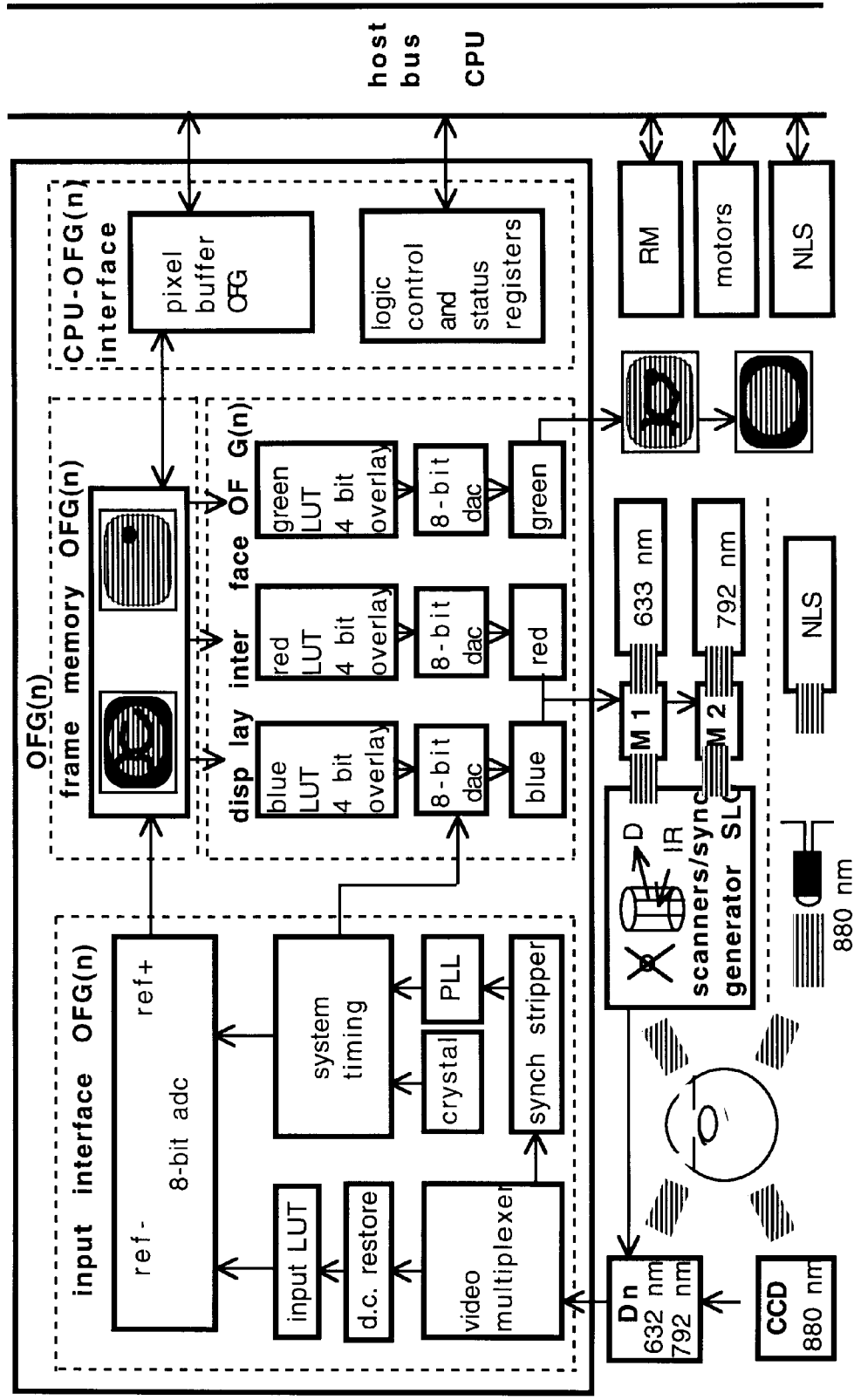

FIG. 4 is a schematic illustrating the architecture of an overlay frame grabber graphics card. It shows the connectivity between the different electronic components of the confocal scanning laser ophthalmoscope, optimized for psychophysical applications. The overlay frame grabber graphic cards have an input interface, frame memory, display interface and CPU interface. Besides the OFG card(s), the host bus accommodates an I/O link for interaction with the control circuits of the motors, radiometer, and Newtonian external light source. The overlay frame grabber card is capable of fast dynamic look-up table switching, input LUT manipulation, non-destructive overlay graphics, two-dimensional gray scale correlation and other pixel calculations in addition to phase locked loop synchronization. The SLO electronics interface shows the synchronization generator, SLO detectors, and modulation options including acousto-optic modulation, neutral density modulation and direct electrical modulation. The following circuits are represented: (1) video-in pathway from detectors and second imaging device. (2) Video-out pathway to monitor. (3) the synchronization pathway and genlocking of the components of the system including analog to digital converter, digital to analog converters, detectors, and modulation. (4) The circuits to and from the motor block, radiometer and Newtonian external light source.

Figure 5:
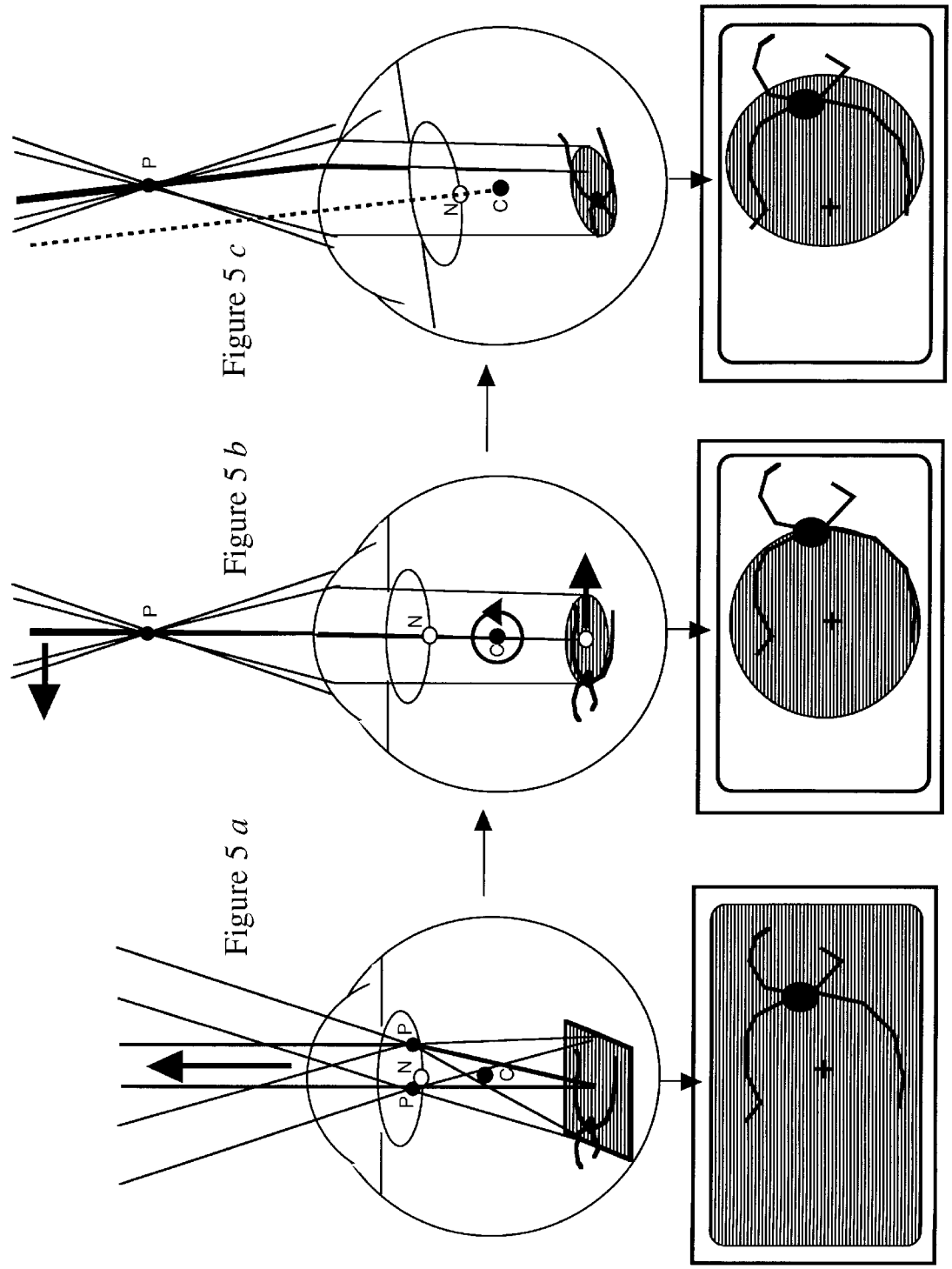

FIG. 5 illustrates the optical ray tracing from the Maxwellian view illumination of the scanning laser ophthalmoscope through the complete schematic eye optics and the mechanism by which it is possible to know, maintain and systematically vary the entrance location of the Maxwellian view for a given retinal location without the need for an external third wavelength light source or external Newtonian second imaging device. In FIG. 5a, the normal situation is depicted wherein the pivot point P of the Maxwellian view illumination is situated near the nodal point N of the complete eye optics. No vignetting is present and the retina is maximally visualized on the monitor. One location in the scanning laser serves as a fixation target for the subject. A lateral movement of the scanning laser laser only, as seen in the picture, will result in a new pivot point of the Maxwellian view. This repositioning may avoid lens changes or other wavefront aberrations while maintaining the laser raster in the same position on the retina, however under a different angle. In FIG. 5b, the pivot point P has been deliberately moved anterior to the eye optics, e.g. about 15 mm, in the imaging focal plane of the complete eye optics. Vignetting by the anatomical pupil now occurs. This creates a blurred rim, clearly visible on the monitor. Anatomical details can be seen within the pupil, i.e. the anatomical pupil is neither homogeneously black or white. The same location in the scanning laser raster serves as a fixation target. The rotational center C of the eye is approximately in the middle of the eye while the nodal point N is situated near the posterior side of the lens. The fixation target is now moved in one direction. FIG. 5c illustrates the results of such movement of the fixation target including the rotation of the eye in order to follow the fixation target, the elliptical transformation and lateral displacement of the pupil, and repositioning of the incoming fixation target rays so that they will enter parallel to the direction in FIG. 5b. These rays however will reach the fixation location under a different angle.

Figure 6:
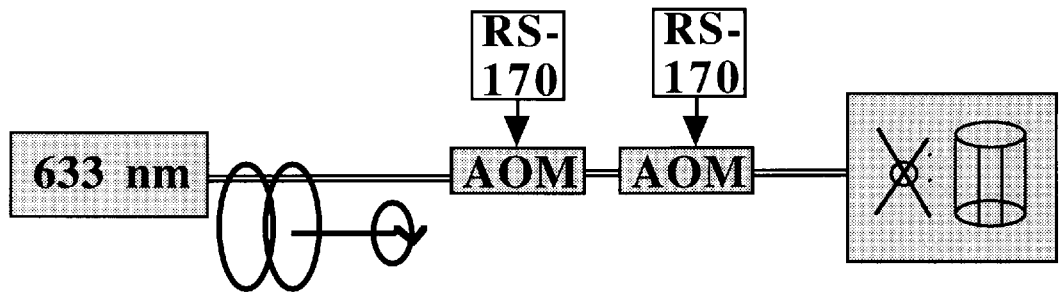
Figure 6:
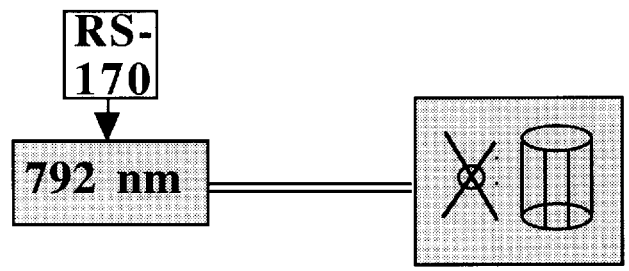
Figure 6:
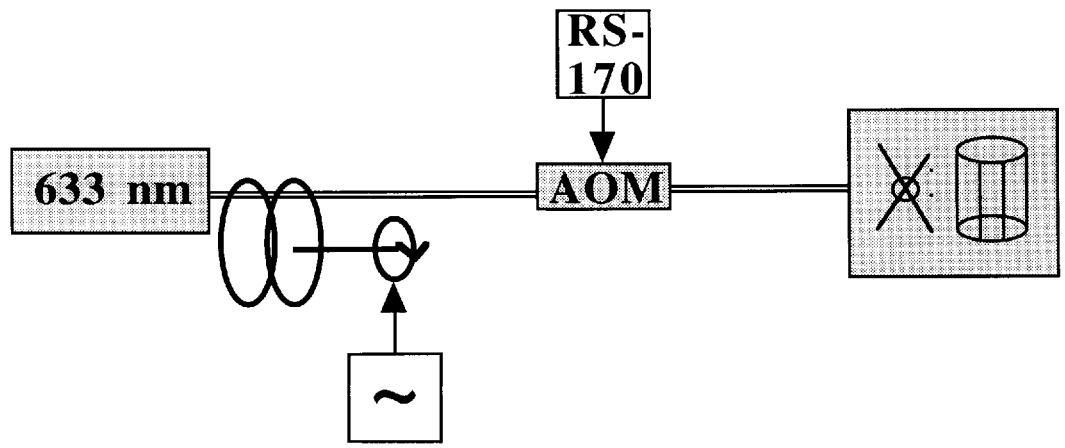

FIG. 6 illustrates different modulation options for the lasers within the scanning laser ophthalmoscope. These include in FIG. 6a a tandem double acousto-optic modulation; FIG. 6b illustrates the electrical amplitude modulation of the diode laser at video rates; FIG. 6c illustrates a continuous modulation with the help of two parallel sheets of polarizers that can rotate relative to each other.

Figure 7:
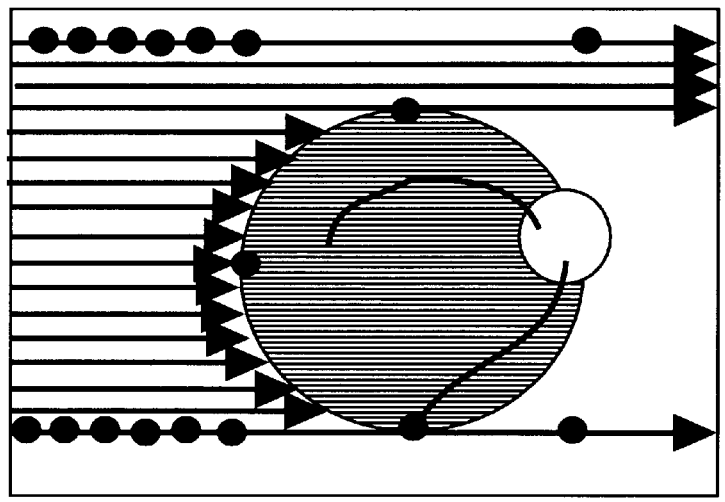
Figure 7:
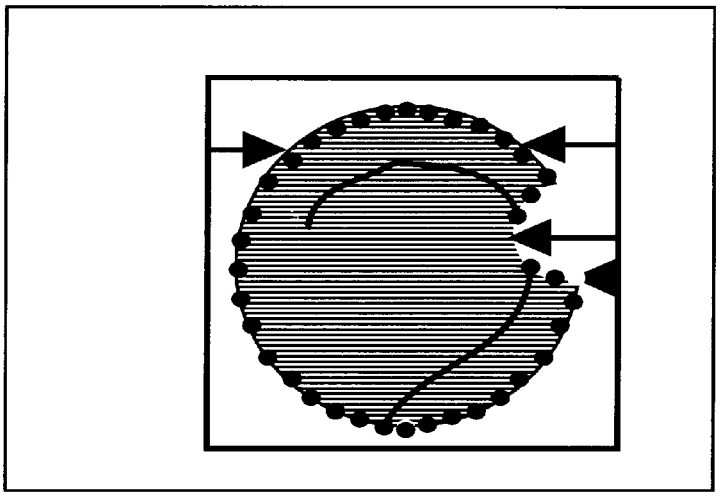
Figure 7:
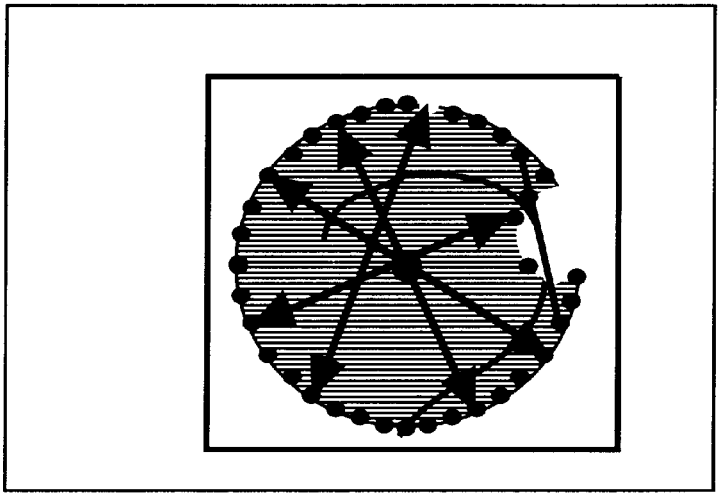

FIG. 7 shows the steps of an algorithm that is used to calculate a central point for an anatomical pupil with blurred rim and retinal details inside.

REFERENCE NUMERALS IN DRAWINGS

10 Prefocussed and Gaussian profile laser beam
12 Posterior pole of the eye
14 Scanners, including polygon and galvanometer driven mirror
16 Pivot point P of the Maxwellian view illumination
18 Collimator-telescope
20 Ocular media including lens and vitreous
22 Backscattered light from the retina
24 Separating mirror
26 Confocal aperture with retinal waist of illuminating beam
28 Avalanche photodiode detector
30 video and synchronization generating circuitry
32 Computer, CPU
34 Overlay frame grabber graphics adaptor card(s)
36 Display monitor
38 Diode infra-red laser
40 Electrical amplitude modulation of diode laser
42 He-Ne laser
44 Pair of rotating linear polarizers
46 Acousto-optic modulator
48 Graphics overlay of stimulus or fixation target
50 Barrier filters, apertures at pupillary conjugate plane
52 Beamsplitter for different wavelengths of lasers 38 and 42
54 Radiometer
56 Beamsplitter separating third wavelength from scanning light sources
58 Barrier filter or masking screen
60 Second Newtonian imaging device
62 Third wavelength external infra-red illuminating source
64 Selective bandpass filter for the third wavelength source 62
66 Videochannel displaying anterior segment, overlay pivot point Maxwellian view or entrance pupil, Purkinje images of third wavelength illumination source if used
68 Motor block enabling xyz positioning of scanning laser ophthalmoscope
70 I/O and control electronics for motorblock, CCD camera, external light source
72 Joystick input for subject's response to psychophysical testing
74 External light source of visible wavelength to provide psychophysical background
76 Rotational center C of the eye
78 Nodal point(s) N of the complete eye optics

DESCRIPTION AND OPERATION OF THE EMBODIMENTS

Two alternative embodiments of related prior art U.S. Pat. No. 5,568,208, with regard to Maxwellian view control in the scanning laser ophthalmoscope, are illustrated in FIG. 2 and FIG. 3. The principles of the scanning laser ophthalmoscope are described in detail in the prior art. Features relevant to the invention are further discussed.

I. THE CONFOCAL SCANNING LASER OPHTHALMOSCOPE

A prefocussed Gaussian beam of laser light 10, e.g. 1.0 mm in diameter, is further focussed by the eye optics, 60 D, to a spot, approximately 10–30μ in diameter at a retinal plane, and this spot is scanned over the posterior pole of the eye 12 in a sawtooth manner with the help of scanning optics, currently a polygon and galvanometer driven mirror 14. Both fast horizontal 15 KHz and slower vertical 60 Hz deflections of the flying laser spot are at standard video RS-170 rates and create the rectangular laser beam raster on the retina. A rectangular area of 0.5 $cm^2$ on the retina is illuminated in the 40 degrees diagonal field of view. A Maxwellian view illumination 16 is used in the scanning laser ophthalmoscope: the pivot point of the scanning laser beam varies minimally in position during scanning and is optimally situated in the plane of the anatomical pupil to minimize wavefront aberrations. The field of view can be changed from 40 degrees to 20 degrees. In the 20 degrees field of view, the pivot point of the Maxwellian view 16 is wider in diameter as the Gaussian beam is doubled in diameter. The amount of prefocussing is adjusted with a collimator-telescope 18 and results in the positioning of the waist of the Gaussian beam at specific planes in the retina. Because of the wider beam in the 20 degree field of view, it is already more difficult to minimize wavefront aberrations by moving the pivot point around focal scattering or absorbing elements in the ocular media 20.

In the confocal scanning laser ophthalmoscope, the light that returns from the retina 22, now distributed in the anatomical pupil, is descanned over the same mirrors and optics, separated from the illuminating beam, mirror 24, and usually passed through a small aperture 26. This aperture, e.g. 1 mm in diameter, is conjugate with a virtual aperture of 100μ at the retinal beam waist. It is used to reduce stray light before the fast and sensitive avalanche photodiode light detector 28. The amount of light that falls on the photodetector is translated into an analog signal by the video and synchronization generating circuitry 30 of the scanning laser ophthalmoscope and this signal is synchronized to the master timing signal provided by the rotating polygon. The video signal is then relayed to the overlay frame grabber graphics cards 32 within the computer 34 which in turn will display the processed signal onto a display monitor 36.

Often two laser sources are aligned to illuminate the retina. The two lasers serve a different purpose. A high intensity diode infra-red 780 nm laser 38, under electrical modulation control 40 and vertically polarized, is nearly invisible to the observer. It produces the retinal image on the display monitor 36. An aligned and low intensity He-Ne 632.8 nm laser 42, horizontally polarized, is modulated with a pair of linear polarizers 44 and acousto-optic modulator 46. The 633 nm laser 42 is used to draw visible graphics in the laser raster. These visible graphics are created by amplitude modulation of the laser 42. For this purpose, the acousto-optic modulator 46 is usually driven by the same computer overlay frame grabber graphics card 34. The graphics, which are seen by the observer, are usually not visible in the retinal image, unless very bright. The exact position and characteristics of the graphics can however be indicated in real-time on the retinal image with the help of computer generated overlays 48 because the image video that comes out of the scanning laser ophthalmoscope and graphics video that modulates the acousto-optic modulator 46 are synchronized to the same timing signals provided by the synchronization generating circuitry 30. The 632 nm He-Ne laser 42, typically used for generating the graphical stimuli at lower intensities, could however also be used for imaging at higher intensity levels.

Multiple and synchronized detectors 28 and multiple laser sources 38,42 have been used before in the original red-yellow krypton color co-pupillary scanning laser ophthalmoscope. Appropriate barrier filters 50, and beamsplitter 52 are necessary, matching the different wavelengths that are used.

Surface-emitting quantum-well laser diodes are of increasing interest, and offer the advantages of high packing densities on a wafer scale. An array of up to a million tiny individually modulated cylindrical $In_{0.2}Ga_{0.8}As$ surface-emitting quantum-well laser diodes, VCLES, with lasing wavelengths in the vicinity of 970 nm and shorter can substitute the traditional laser sources 38, 42 and scanners 14 if coupled with a two-dimensional detection array. The use of such a specific extended detection array has been discussed in the original U.S. Pat. No. 4,213,678.

An additional combination of aperture with filter 50 can be positioned after descanning the returning light in the neighborhood of a pupillary conjugate plane, for example a photodetctor 28. If small apertures are used, then the exit pupil of the returning light will be made smaller and therefore represent the backscattered light having the direction of the illuminating laser. This property is used in combination with a small aperture 26 for reflectometric measurements. Applications are in the field of Stiles-Crawford, photopigment and wavefront aberration measurements.

II. LASERS AND THEIR MODULATION OPTIONS FOR THE SCANNING LASER OPHTHALMOSCOPE

The 632.8 nm He-Ne laser 42 has been incorporated in the scanning laser ophthalmoscope in part because of its compact design and superior Gaussian beam characteristics. It is also the wavelength of choice for many psychophysical applications. Reasons for this preference are the maximal transmittance and minimal scatter within the transparent media of the eye 20, a minimal interference with the xanthophyll and hemoglobin pigments, and a monophasic psychophysical cone response. These advantages are not available with shorter visible wavelengths but are still present if a longer visible wavelength were chosen, e.g. a diode laser wavelength of 650 nm. The output of the He-Ne laser is polarized. In many psychophysical applications that require a control of the Maxwellian view entrance location it is equally important to have a modulation control that can continuously change the intensity of a small test stimulus on a specific retinal location from a very high value to zero value without the interference of a visible background illumination in the neighborhood of the retinal location being tested. Absolute threshold measurements require such a zero background illumination and high resolution intensity scale. The visible background illumination corresponding to the retinal location of a test stimulus is either produced by the dim but still visible infra-red scanning laser raster used for generating the retinal image, or by the same scanning laser that also produces the test stimulus. Several strategies can be employed to reduce both background light intensities to zero value.

The diode laser most often used in the scanning laser ophthalmoscope has a wavelength around 792 nm, because this wavelength can also be used for indocyanin green angiographies. Longer wavelengths, e.g. 904 nm are commercially available. For every 10 nm increase in wavelength of the diode laser beyond 670 mm, the efficiency for stimulating the retina psychophysically will be reduced to one-half. This is useful in making the background infra-red scanning laser raster even less visible to the subject. Another possibility exists to minimize the infra-red laser background in the neighborhood of the retinal location being tested and is illustrated in FIG. 6b. It is possible to use one of the output video channels of the overlay frame grabber to control the amplitude modulation 40 of the diode laser. Even if the bandwith of modulation is somewhat lower than true RS-170 video, the infra-red laser raster intensity can be reduced to a minimum intensity in the neighborhood of the location being tested. Obviously, the retinal image on the monitor will be defective in that area since no infra-red illumination is present. However the larger part of the retinal image will still be visible and this is sufficient.

Traditional cupola perimeters such as the Goldmann perimeter, employ a Newtonian illumination system, and the psychophysical stimulus and background illumination are provided through different optical paths, the light source however being the same. There is a major advantage to this configuration. Additional separate modulation of background and test stimulus is possible with the help of neutral density filters and it is therefore possible to obtain a truly zero background intensity by blocking the path of the background illumination, while a maximum stimulus is still provided by the other path. Unlike the Goldmann perimeter, a stimulus and a background illumination are provided together by the same optical path and laser light source in the scanning laser ophthalmoscope, and cannot be modulated with separate means independently from each other. A truly zero background combined with a maximum intensity stimulus is therefore not possible because the maximum ratio between stimulus and background cannot be increased. For acousto-optic modulation, the theoretical maximum ratio is about 700, a ratio of 300 is a practical and desired limit, but very often only a ratio of 100 is obtained. A special way of increasing this ratio is to combine in tandem two acousto-optic modulators 46 (FIG. 6a). Each of the acousto-optic modulators are controlled by the output of a video-channel of the graphics card. This two-dimensional modulation can therefore generate a ratio of at least 10,000 between test stimulus and background and can generate the $256^2$ levels in between. This results in an adequate high resolution scale, maximum stimulus and minimal background illumination for measuring absolute thresholds.

Another approach, exemplified in FIG. 6c, uses one acousto-optic modulator 46 that is only used for setting the maximum ratio between stimulus and background and not for generating the levels in between. The levels in between are generated by a continuous modulation means 44 consisting for example of two parallel polarizing sheets that can rotate relative to each other. The rotation again is under control of a output video channel of the graphics card. A neutral density filter effect is created that acts both on the background and stimulus intensity. With other words, it is possible to reduce continuously the intensity of the test stimulus from a maximum to a minimum value and having the assurance that the associated background will be reduced in an equal amount. This means that if the stimulus threshold for a given retinal test location is low, the background in the neighborhood of that retinal location being tested will be correspondingly lower and close to zero value. If the stimulus threshold were high, then the correspondingly higher, but still minimal background would not matter either.

Calibration curves for the previous modulation options are obtained using a microprocessor controlled laser radi-ometer 54, for example the "lasercomp" from EG&G GammaScientific, Inc, San Diego, Calif. Calibration is traceable to the National Institute of Standards Technology and in complete compliance with MIL-STD-45662A. The silicon detector with an area of 100 sq. mm is connected through a RS-232 serial interface to the same computer 32 that controls the diverse modulating means. The detector is attached to the scanning laser ophthalmoscope. Stray light is eliminated. The beamsplitter 56 diverts a percentage of the scanning laser raster to the radiometer 54. An optional and variable barrier filter or masking screen 58 can be inserted. Methods for obtaining the calibration curves are detailed in the prior art.

III. MAXWELLIAN VIEW CONTROL OPTIONS

The embodiments of FIGS. 1, 2, and 3 are for use with the Rodenstock Scanning Laser Ophthalmoscope 101 or 102 (Munich, Germany). They are readily adapted for other scanning laser ophthalmoscopes by s/he who is skilled in the art.

FIG. 1 describes the prior art of related U.S. Pat. No. 5,568,208. A second Newtonian imaging device 60, beamsplitter 56, third wavelength wide angle illumination source 62, and appropriate filter 64 are attached in a fixed position to a confocal scanning laser ophthalmoscope with several modulating means 40, 44, 46 for the lasers. The CPU-OFG combination 32, 34 is capable of fast two-dimensional gray scale correlation or other digital image processing techniques in order to retrieve the position of the anterior segment relative to the entrance location of the Maxwellian view of the scanning laser ophthalmoscope. The anterior segment is visualized on the monitor 66, free as much as possible of spurious reflexes caused by the scanning illuminating light sources, especially the strong infra-red scanning laser source of the scanning laser ophthalmoscope. The anatomical pupil is typically dark under these conditions, and has usually a fixed diameter because of a medical dilation. The anterior segment image shows anatomical structures and Purkinje images that can serve as fiducial landmarks for a pattern recognition algorithm such as two dimensional gray-scale correlation. Other digital image processing techniques, that are simpler, can perform equally well and are described in a later section. The movement of the anterior segment relative to the scanning laser ophthalmoscope is registered by recognizing the fiducial landmarks on a continuous basis. The coordinates of the location of the pivot point of the Maxwellian view are known in the images because of a prior calibration onto the anterior segment of the eye. This calibration is performed without a total barrier filter, to permit the moderate backscatter from the lens and iris of the attenuated illuminating lasers of the scanning laser ophthalmoscope to reach second imaging device 60. This location can then be overlayed on the image of the anterior segment when the barrier filter 64 is present. The actual position of the pivot point inside the eye is slightly different from the position of the pivot point in free air because of the refractive properties of the cornea, and this minimal difference also depends on the actual position of the pivot point in the eye. This difference can be mapped as mentioned before by focussing on a sheet of paper first and then on the iris or anterior surface of the lens through the cornea. Also Purkinje images, if used, can move relative to the other fiducial landmarks. These differences in location are usually minimal and can also be easily calculated or mapped prior to testing.

A motor block component 68, capable of moving the SLO in the x-y-z directions is connected to the computer 32 with the help of a I/O control circuitry 70. This motor block 68 can receive feedback from the pattern recognition algorithm, equivalent algorithm or autofocus lens of second imaging device, and thereby maintain or systematically vary the entrance location of the Maxwellian view in the anatomical pupil. In order to overcome potential problems with the recognition of features in the anterior segment of the eye in the presence of a variable pupil and specifically to measure pupil characteristics such as size, the means of related U.S. patent can be used, however without the external third wavelength illuminating source 62 and barrier filter 64. This method solely relies on the strong retinal backscatter through the anatomical pupil from the illuminating sources of the scanning laser ophthalmoscope 38, 42 themselves.

In FIG. 2 the third wavelength wide angle external illuminating source 62 and barrier filter 64 are absent. The monitor 66 illustrates an anterior segment image taken with the second Newtonian imaging device 60. The infra-red laser 38 of the scanning laser ophthalmoscope illuminates the posterior pole 12 of the eye. The unattenuated returning light from the retina 22 will now fill the complete anatomical pupil. This pupil is therefore seen homogeneously white on an otherwise dark background, and in sharp focus. The pupil size can be variable. The white pupil image itself conceals any spurious reflexes that may exist, e.g. the Purkinje images or direct backscatter from the iris and anterior surface of the lens of the eye. The pupil diameter however has to be larger than the entrance location of the Maxwellian view illumination of the scanning laser ophthalmoscope, and this entrance location preferably stays well within the rim of the anatomical pupil. This is necessary for the simplest pattern recognition algorithm to work in a reliable fashion. Such a digital processing algorithm calculates the number of white pixels in the video image in order to to have an idea of the size of the pupil. The location of the white pupil can be defined as its centroid. This is also easily calculated.

FIG. 3 illustrates a further variation of FIG. 1 in which is noted not only the absence of the third wavelength wide angle external illuminating source 62, but also the second Newtonian imaging device 60. The second Newtonian imaging device can be replaced with a preferably Newtonian and regulated external light source 74, in the visible range of the wavelength spectrum. Its purpose is to provide an additional uniform background illumination on the posterior pole 12 of the eye for some psychophysical experiments. If the source 74 is Newtonian, then the pupil size must be known in order to calculate the retinal background illumination in Trolands. Small variations in pupil orientation can usually be neglected.

Importantly, the pivot point 16 of the Maxwellian view illumination of the scanning laser ophthalmoscope has been replaced in front of the eye. Vignetting of the anatomical pupil is then visible on the monitor 66. This anatomical pupil has a blurred but regularly curved margin on the monitor 66 and contains some retinal details i.e. the inside of the anatomical pupil is not homogeneously bright or dark. The area on the monitor outside the pupil is however black. Some noise pixels may also be present. Most often the pupil will be dilated. The pupil margin is blurred because the beam diameter of the illuminating laser 38 is still much larger than the waist at the retinal plane.

FIG. 5 illustrates the ray tracing from the Maxwellian view illumination of the scanning laser ophthalmoscope through the complete schematic eye optics and the important mechanism by which it is possible to know, maintain and systematically vary the entrance location of the Maxwellian view for a given retinal location without the need for an external third wavelength light source 62 or additional Newtonian second imaging device 60. In FIG. 5a, the normal use of operation of a scanning laser ophthalmoscope is illustrated, wherein the pivot point P 16 of the Maxwellian view illumination is situated near the nodal point N 78 of the complete eye optics. No vignetting by the rim of the anatomical pupil occurs, i.e. the retina is maximally visualized on the monitor. One location in the scanning laser raster serves as a fixation target. Another location in the neighborhood will serve as test location for the subject. A lateral movement of the scanning laser laser only, as illustrated, will result in a new pivot point P of the Maxwellian view. This repositioning may be necessary to avoid lens changes or other wavefront aberrations while maintaining the laser raster in the same position on the retina, however viewing the retina under a different angle. In FIG. 5b, the pivot point P has been deliberately moved anterior to the eye optics, e.g. about 15 mm, and positioned in the imaging focal plane of the complete eye optics. Other positions of the pivot point P are possible, even further inside the eye. Vignetting by the anatomical pupil now occurs. This creates a blurred rim of the anatomical pupil, clearly visible on the monitor. Within the rim anatomical details can be seen, i.e. the anatomical pupil is neither homogeneously black or white. The same location in the scanning laser raster however serves as a fixation target or test location. It is important to note that the rotational center of the eye C 76 is approximately in the middle of the eye while the nodal point N is situated near the posterior side of the lens, i.e. about 6 to 7 mm anterior to C. The individual rays of the scanning laser raster reach the retina in an approximate conical configuration, a cylinder if the pivot P is situated in the imaging focal plane of the eye optics. A conical section with the iris plane creates the margin of the anatomical pupil that is seen on the monitor. The fixation target is now moved in one direction by the algorithm of the instrument. The subject is instructed to follow the fixation target. FIG. 5c illustrates the results of such movement of the fixation target. As the fixation target moves laterally, the eye will rotate, not around the nodal point N but around the center of the optics C. As a result, the bundle of rays that creates the fixation target in FIG. 5b will remain parallel to the incoming rays that create the fixation target in FIG. 5c, except for very small angulations induced by local wavefront aberrations. These incoming rays however will reach the fixation target under a different angle, which is precisely the purpose of the proposed algorithm. On the monitor it can be seen that the initial rim of the anatomical pupil will shift in the opposite direction of the movement of the fixation target by a small amount. Also the anatomical pupil will become elliptical in a small amount predicted by the conical sectioning. These changes have to be taken into account when representing the entrance locations of the Maxwellian view on a single frontal image of the anatomical pupil. The aberrations within the anatomical pupil would have to be known if an absolute representation is to be made. Such wavefront mapping can be accomplished with another scanning laser ophthalmoscope. The conical sections can be completely defined, if necessary, by measuring on forehand the position of focal, nodal and principal points of the eye optics with other techniques that are well known in ophthalmology. These techniques include ultrasound biometry, keratometry and automated refraction. In summary, this technique replaces the systematic movements of the scanning laser ophthalmoscope and subject relative to each other with the rotations of the eye itself, thereby reducing considerably the complexity of such instruments that determine Stiles-Crawford effects. The problem of determining the anatomical rim and center of the anatomical pupil when the pupil rim is blurred and possibly irregular will be dealt with in the next chapter.

If the test location is further away from the fixation area on the retina, then it becomes impossible to move systematically the entrance pupil of the test location to all locations within the anatomical pupil. Some locations cannot be used because the fixation target would fall outside the rim of the anatomical pupil in these situations. The problem is solved by increasing the light intensity of the fixation target for these locations Higher intensity fixation targets will then easily penetrate the masking iris and reach the retina.

IV. DIGITAL IMAGE PROCESSING, FUNDUS AND PUPIL TRACKING

An overlay frame grabber graphics card or equivalent, schematized in FIG. 4, is indispensable for processing the video that is generated by the scanning laser ophthalmoscope diagnostic laser sources or second imaging device, and for the production of graphics that will be projected onto the retina. For the applications an Imaging Technology OFG card in a regular pentium chip based PC is used. This overlay frame grabber graphics adaptor can accept four different video input sources, and digitizes the incoming video signals to eight bits of accuracy, at a rate of 60 fields per second (RS-170 video). On-board frame memory can store two 512 by 480 pixel video frames or one larger 768 by 512 pixel video frame. Two or more overlay frame grabber adaptors, which are I/O mapped, can reside in one computer. This versatility is important for the concurrent analysis of signals from a multidetector scanning laser ophthalmoscope and other imaging devices.

The analog-to-digital converter of the frame grabber adaptor has programmable negative and positive reference values for calibrating the white and black video signal levels. A look-up table (LUT) controls the input video and can be used for preprocessing contrast and intensity. This feature is useful in facilitating digital image processing techniques such as normalized gray scale correlation or outlining the rim of the anatomical pupil as further explained.

An additional four bits per pixel control the instantaneous switching between 16 different output look-up tables for each pixel. This process is known as dynamic look-up table switching. Three independent output video channels are provided for each imaging adaptor. The output channels generate RS-170 video adapted for the purpose of pseudo-color display. Output LUT programming is a well known solution for creating non-destructive graphic overlays. Non-destructive graphic overlays drawn over the incoming video signal generate the stimuli visible in the laser raster of the scanning laser ophthalmoscope and are used to indicate the retinal position of the stimuli and fixation target on the display monitor. In FIG. 4, the green output video-channels send the images of the detectors and second imaging device to the monitor; these images are overlaid with graphics indicating the fixation target, stimulus location, center of anatomical pupil. The blue or red output channels of the original video signal are transformed into a graphics pattern that represents the stimulus and fixation target. These video channels control the different modulating means and define what is visible to the observer in the scanning laser ophthalmoscope. Another important feature of the overlay frame grabber adaptor is the capability to synchronize to an external video source using a phase-locked loop. This is important since the master timing signal of the electronics is provided by the high speed rotating polygon.

As mentioned before, digital image processing techniques are used for the tracking of fiducial landmarks in the retinal image and for locating the anatomical rim of the pupil in the two different ramifications of the invention. The overlay frame grabber card can perform these tasks using for example a technique called two-dimensional normalized gray-scale correlation. The software that instructs the graphics adaptor to perform such algorithms is provided by Imaging Technology, Inc, Bedford, Mass. In two-dimensional normalized gray-scale correlation a characteristic search pattern, such as Purkinje images and other anatomical landmarks of the anterior eye segment are located within the video images provided by second imaging device. The pattern recognition algorithm by means of the OFG adaptor has a 7 degree rotational tolerance and an optimal 60 ms search time, adequate performance for many psychophysical testing procedures.

If the anatomical pupil is homogeneously white on a uniform black background, with little artefacts, a simpler image processing algorithm is possible. It calculates the number of white pixels in the image and determines the center of mass of such pixels. The outline of the anatomical pupil can be defined as the collection of neighboring pixels that switch from black to white or white to black for each video line. Many alternative approaches are possible. Correction for a lowering upper eyelid has to be build in. If the anatomical pupil contains retinal detail and if this pupil also has blurred margins, a more elaborate approach has to be taken as illustrated in FIG. 7. The most significant complication is that part of the optic disc area will show at times at the rim of the anatomical pupil. Some pixels belonging to the optic disc may be black and therefore confuse with the black surrounding of the anatomical rim. In FIG. 7a, the most likely positioning of the anatomical pupil is found by scanning every n number of video lines every m pixels for p adjacent pixels that are not black or near black. Very few pixel readings are necessary to locate approximately the pupil within the complete video image. In FIG. 7b the algorithm is further limited to a square that surrounds the most likely anatomical pupil location. At this point the same algorithm is repeated from both side with a higher resolution. Thus a number of pixel locations can be found that are the outer pixels of the anatomical rim, with the notable exception of dark pixels that belong to retinal details such as the optic disc. These false pixels can be eliminated by either looking for the largest diameter between all possible pixel combinations constituting the rim of the pupil, or by eliminating those pixels that would fall on a chord segment between any two pixels belonging to the rim of the pupil as illustrated in FIG. 7c.

Again, corrections have to be made for a lowering upper eyelid. This can be accomplished by reconstructing the upper part of the rim of the anatomical pupil with information from the inferior half and previous images where the pupil border was complete. The time consuming part of the algorithm is the communication between the graphics adaptor I/O means and the CPU. These interactions have been kept to a minimum in the algorithm. The result is a well-defined localization of the anatomical rim and a sufficiently accurate estimate of the center of the anatomical pupil as seen on the monitor. Real-time tracking is possible with the algorithm. The algorithm works in case of variable pupil diameters and can even be used in combination with the two-dimensional pattern recognition explained earlier. In this case the anatomical pupil would appear black and all surrounding pixels any value except black. Size variations of the fiducial landmarks are useful for measuring antero-posterior movements.

One practical application of the embodiment that is capable of knowing and maintaining simultaneously the entrance location of the Maxwellian view and the retinal location being tested is the automated pupillometer. This device can measure the changing characteristics of the pupil when a specific stimulus is projected onto the retina, typically at the foveal location. In practice, the retina is observed on a monitor while the subject is instructed to look at a faint fixation target or simply straight ahead. The background is set to minimum using the modulation options that have been described. The pupil characteristics, especially size of the pupil are constantly monitored with the algorithm described earlier. A bright stimulus of known size, duration, retinal location and intensity is then projected onto the retina and the changing anatomical pupil characteristics are being recorded by grabbing all video with a PCI frame grabber card. The further mathematical analysis of the data is straightforward and well-known in the prior art.

An application of the embodiment that is capable of knowing, maintaining and systematically varying the entrance location of the Maxwellian view while keeping the retinal location to be tested constant, is the determination of Stiles-Crawford parameters for that particular testing location on the retina. This test can be based on the measurement of incremental perimetric static thresholds for that location, fully light-adapted, using the additional Newtonian light source to provide the necessary homogeneous background. The other approach is to measure absolute retinal static thresholds under dark-adapted conditions and making sure that no stray light or visible background illumination is present. This method has the advantage that it not only measures the direction and degree of directionality of photoreceptors but also estimates their pigment content. The modulation techniques that have been described earlier are used for this purpose. The retinal thresholds themselves are measured using a variety of existing techniques. The preferred algorithm for estimating retinal sensitivity uses an adaptive yes-no strategy wherein adjustable steps are determined by immediately preceding trials. The algorithm is modelled after Taylor & Creelman's "parameter estimation by sequential testing" or PEST. Several variations, maximizing the efficiency of data gathering and analysis are known in the prior art or are obvious to the persons skilled in the art of psychophysical testing.

The procedure is summarized as follows. Background method is selected. A fixation target, e.g. a small circle wherein the static test stimulus will be presented, is shown to the subject for pure foveal locations. Its intensity should be kept slightly suprathreshold throughout the test. The parameters of the stimulus, such as size and duration are selected. Example values are 20 min arc on a side and 0.1 s. The static thresholds are determined using the selected algorithm for every significant entrance location of the Maxwellian view using the method of displacing the fixation target as outlined before. The Stiles-Crawford parameters, location and peakedness are then computed from a quadratic curve fitting of the collection of static thresholds over the pupillary area. The fixation stability of the subject can be verified before and after every stimulus stimulus presentation using the two-dimensional grayscale pattern recognition algorithm on retinal landmarks. It is also possible to give real-time feedback regarding the position of the anatomical pupil so that the selected entrance location of the Maxwellian view is indeed the one that is used for the thresholding operation. Thus, the use of a dental bite can be avoided.

The 632.8 nm He-Ne laser is a wavelength of choice for measuring the Stiles-Crawford parameters. Reasons for this preference are as mentioned before, the maximal transmittance and minimal scatter within the transparent media of the eye, a minimal interference with the xanthophyll and hemoglobin pigments, and a monophasic psychophysical cone response. Retinal cone thresholds reach a stable plateau after some minutes of dark-adaptation following an exposure to light that will eliminate rod intrusion during the subsequent measurements. The dynamic scale of stimulus intensities should be between 2.5 log units and 3 log units. The methods to obtain such a range have been discussed. In the 40 degree field of the scanning laser ophthalmoscope, a foveal stimulus of 20 min arc on a side equivalent to 6 adjacent pixels or $100\mu$ is used. This stimulus will reach a foveal cone population of about 4000 assuming the intercone distance to be $1.8\mu$. If an entrance Gaussian beam waist of 0.5 mm radius is used and assuming the image focal length f' of the eye to be 22.8 mm, the diameter of the focussed flying spot on the retina will be about $17\mu$. This is a perfect match for a pixel of the same size assuming 3.4 min arc per pixel calibration. The wavefront of the stimulus will be flat when reaching the photoreceptors. Also a large depth of focus, a Rayleigh zone exceeding $500\mu$ is available with the selected entrance beam. The entrance beam diameter of less than 1.0 mm will usually avoid problems with localized wavefront aberrations in the dioptric media and yields an optimal resolution at the anatomical pupil of the eye. An optical reflectometric equivalent for measuring the Stiles-Crawford parameters can be realized by using the above methods with the selective detection and measurement of the returning light using a small aperture at a pupillary conjugate plane. This can also be done under bleached and non-bleached conditions to get an idea of the available photopigment.

Recent evidence suggests that both anatomical cone types and rods exhibit high intrinsic directionality, however further quanta absorption by neighboring photoreceptors of scattered photons and spatial summation properties of pooled photoreceptors can explain the highest psychophysically measured directionality for cones at 1 degree of eccentricity on the retina, somewhat lower directionality at the central foveola and absent directionality for rods.

Although the description above contains many specificities, these should not be construed as limiting the scope of the embodiments of the invention but as merely providing illustrations of some of the presently preferred embodiments of this invention. Other embodiments of the invention including additions, subtractions, deletions, or modifications of the disclosed embodiment will be obvious to those skilled in the art and are within the scope of the following claims. The scope of the invention should be determined by the appended claims and their legal equivalents, rather than by the examples given.

I claim:

1. A scanning laser ophthalmoscope with Maxwellian view control for imaging and functional testing of the eye, comprising of:

(A) a scanning laser ophthalmoscope, using Maxwellian view illumination for illuminating lasers of which at least one will have a wavelength in the visible range of the spectrum and another will have a wavelength in the infra-red range of the spectrum; said wavelengths useful for visualizing the posterior segment of the eye and functional testing of the eye; said scanning laser ophthalmoscope further equipped with means for modulating said lasers, and having electronic means for generating video and controlling said modulating means;

(B) a second imaging device using Newtonian viewing and beamsplitter, for visualizing the anatomical pupil of the anterior segment of the eye, said beamsplitter having specific coatings and orientation with regard to said scanning laser ophthalmoscope and said second imaging device, as to permit a continuous high quality observation of the posterior segment of the eye with said scanning laser ophthalmoscope, simultaneously with an observation of the backscatter of said illuminating lasers from the posterior segment of the eye through the anatomical pupil of the anterior segment of the eye with said second imaging device;

(C) a computer with at least one imaging adaptor capable of overlay graphics, for controlling said modulating means and displaying on a monitor the image of the posterior segment of the eye with overlays indicating characteristics of any psychophysical stimuli produced by said illuminating lasers; said computer with imaging adaptor further capable of analyzing the video produced by said second imaging device using digital image processing algorithms; whereby said digital image processing of the video produced by said second imaging device will indicate the size of said anatomical pupil and also the location of said anatomical pupil relative to the position of said scanning laser ophthalmoscope during functional testing of the eye.

2. A method for controlling the Maxwellian view entrance location of a scanning laser ophthalmoscope during imaging or functional testing of the retina of an eye comprising the steps of:

(A) positioning the scanning laser ophthalmoscope relative to the eye in such manner that vignetting occurs by the rim of the anatomical pupil of the eye, said anatomical pupil now completely visible on a video image produced by said scanning laser ophthalmoscope, simultaneously with part of the retina of said eye;

(B) using illuminating means and modulating means of said scanning laser ophthalmoscope to create a fixation stimulus for controlling the orientation of the eye and choosing a retinal test location for further reflectometric or psychophysical measurements;

(C) using a computer capable of digital image processing to determine repeatedly the location of the rim of the anatomical pupil with regard to the entrance location of said fixation stimulus and said retinal test location, also determining the absolute location of said rim of the anatomical pupil in the video image produced by said scanning laser ophthalmoscope;

(D) positioning said fixation stimulus with the help of said modulating means in an initial location within the boundary provided by said rim of the anatomical pupil using the information provided by said step C and then at different locations according to an algorithm and using the information provided by said step C, while measuring the characteristics of the retinal test location for reflectometric or phsycophysical purposes with the help of said modulating means;

whereby it becomes possible to know, maintain and systematically vary the Maxwellian view entrance location of said retinal test location within the boundary provided by said rim of the anatomical pupil for the purpose of measuring the influence on imaging and functional testing of variations of said entrance location, said retinal test location receiving light from the illuminating means of said scanning laser ophthalmoscope from different angles of incidence in an algorithmic, predictable and measurable fashion, further eliminating the need for external imaging devices to detect said entrance location of the Maxwellian view, and not having to actively move the scanning laser ophthalmoscope relative to retinal test location in order to select a different entrance location of the Maxwellian view for said retinal test location.

3. A scanning laser ophthalmoscope with Mazwellian view control for imaging and functional testing of the eye, according to claim 1, having second modulating means for said illuminating lasers, and using same said at least one imaging adaptor for controlling said second modulating means, whereby the combined effect of said modulating means and said second modulating means minimizes the intensity of the visible background produced by said illuminating lasers while mazimizing the ratio of stimulus intensity to the background intensity during functional testing of the eye.

4. A method for controlling the Maxwellian view entrance location of a scanning laser ophthalmoscope during functional testing of the retina of an eye, according to claim 2, comprising the additional use of a second modulating means in said scanning laser ophthalmoscope to minimize the intensity of the visible background produced by said illuminating means while maximizing the ratio of stimulus intensity to the background intensity during functional testing of the eye for any given combination of said retinal test location and said entrance location within the boundary of the anatomical pupil.

* * * * *